(12) United States Patent
Kast et al.

(10) Patent No.: US 7,805,200 B2
(45) Date of Patent: *Sep. 28, 2010

(54) IMPLANTABLE MEDICAL DEVICE WITH EXTERNAL HOUSING FOR A RECHARGING COIL

(75) Inventors: John E. Kast, Hugo, MN (US); Oscar Jimenez, Coral Gables, FL (US); Charles E. Peters, Blaine, MN (US); James E. Riekels, New Hope, MN (US); Mark E. Schommer, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 915 days.

This patent is subject to a terminal disclaimer.

(21) Appl. No.: 10/772,944

(22) Filed: Feb. 5, 2004

(65) Prior Publication Data

US 2004/0267332 A1 Dec. 30, 2004

Related U.S. Application Data (63) Continuation of application No. 09/596,566, filed on Jun. 19, 2000, now abandoned.

(51) Int. Cl.
*A61N 1/372* (2006.01)
(52) U.S. Cl. ............................................. 607/61
(58) Field of Classification Search ............. 607/33, 607/35, 61, 34, 36, 37, 55, 56, 57, 30, 60; 128/903
See application file for complete search history.

(56) References Cited

U.S. PATENT DOCUMENTS

| | | | |
|---|---|---|---|
| 3,357,434 A | 12/1967 | Abell | |
| 3,667,477 A * | 6/1972 | Susset et al. | 607/40 |
| 3,824,129 A * | 7/1974 | Fagan, Jr. | 607/33 |
| 3,888,260 A | 6/1975 | Fischell | |
| 4,041,955 A | 8/1977 | Kelly et al. | |
| 4,071,032 A | 1/1978 | Schulman | |
| 4,134,408 A | 1/1979 | Brownlee et al. | |
| 4,186,749 A | 2/1980 | Fryer | |

(Continued)

FOREIGN PATENT DOCUMENTS

EP     0 811 395 A2     12/1997

(Continued)

OTHER PUBLICATIONS

Medtronic, Inc., "Implantable Neurostimulation Systems", 1998.

(Continued)

*Primary Examiner*—Carl H Layno
*Assistant Examiner*—Frances P Oropeza
(74) *Attorney, Agent, or Firm*—IPLM Group, P.A.

(57) ABSTRACT

A rechargeable implantable medical device with an external recharging coil carried on the medical device proximal face. The recharging coil can be attached to the medical device housing physically, or chemically, or a combination of both physically and chemically. The recharging coil electrically couples through housing electrical feedthroughs to electronics configured to perform a therapy and a rechargeable power source both carried inside the medical device housing. Additionally methods for attaching the external recharging coil to an implantable medical device are disclosed. The rechargeable implantable medical device can be a medical devices such as a neuro stimulators, drug delivery pumps, pacemakers, defibrillators, diagnostic recorders, cochlear implants, and the like.

21 Claims, 10 Drawing Sheets

U.S. PATENT DOCUMENTS

| | | | |
|---|---|---|---|
| 5,190,034 A * | 3/1993 | Sholder | 607/5 |
| 5,279,292 A * | 1/1994 | Baumann et al. | 607/137 |
| 5,314,457 A | 5/1994 | Jeutter et al. | |
| 5,411,537 A | 5/1995 | Munshi et al. | |
| 5,527,348 A | 6/1996 | Winkler et al. | |
| 5,562,714 A | 10/1996 | Grevious | |
| 5,613,935 A | 3/1997 | Jarvik | |
| 5,690,693 A | 11/1997 | Wang et al. | |
| 5,713,939 A | 2/1998 | Nedungadi et al. | |
| 5,733,313 A | 3/1998 | Barreras, Sr. et al. | |
| 5,861,019 A | 1/1999 | Sun et al. | |
| 6,067,474 A * | 5/2000 | Schulman et al. | 607/57 |
| 6,154,677 A * | 11/2000 | Leysieffer | 607/61 |
| 6,178,353 B1 | 1/2001 | Griffith et al. | |
| 6,275,737 B1 | 8/2001 | Mann | |
| 6,308,101 B1 | 10/2001 | Faltys et al. | |
| 6,324,430 B1 | 11/2001 | Zarinetchi et al. | |
| 6,505,077 B1 * | 1/2003 | Kast et al. | 607/61 |
| 6,516,227 B1 | 2/2003 | Meadows et al. | |
| 2002/0084881 A1 * | 7/2002 | Kummel | 336/200 |

FOREIGN PATENT DOCUMENTS

| | | |
|---|---|---|
| EP | 1 048 324 A2 | 11/2000 |
| WO | WO 98/37926 | 9/1998 |
| WO | WO 99/06108 | 2/1999 |
| WO | WO 99/44684 | 9/1999 |
| WO | WO 00/01442 | 1/2000 |
| WO | WO 01/83029 A1 | 11/2001 |
| WO | WO 01/97908 A2 | 12/2001 |
| WO | WO 01/97908 A3 | 12/2001 |

OTHER PUBLICATIONS

Sinha, Gunjan, "The Heart, Medicine & Health", Popular Science, p. 43, Feb. 2000.

Medtronic, Inc., "Mattrix Neurostimulation System", Brochure, 1995.

* cited by examiner

IMPLANTABLE MEDICAL DEVICE WITH EXTERNAL HOUSING FOR A RECHARGING COIL

CONTINUING APPLICATION AND CLAIM OF PRIORITY

This patent application is a continuation of U.S. patent application Ser. No. 09/596,566, filed Jun. 19, 2000, now abandoned.

CROSS REFERENCE

The present application is related to the following applications entitled "Implantable Medical Device With External Recharge Coil Electrical Connection" by inventors Kast et al. (U.S. patent application Ser. No. 09/596,211 filed Jun. 19, 2000, now U.S. Pat. No. 6,505,077) and "Implantable Medical Device With Recharging Coil Electro-Magnetic Shield" by inventors Kast et al. (U.S. patent application Ser. No. 09/596,402 file Jun. 16, 2000, now U.S. Pat. No. 6,850,803), which are not admitted as prior art with respect to the present invention by its mention in this cross reference section.

BACKGROUND OF THE INVENTION

This disclosure relates to implantable medical devices and more specifically to a rechargeable implantable medical device with an external recharging coil.

The medical device industry produces a wide variety of electronic and mechanical devices for treating patient medical conditions. Depending upon medical condition, medical devices can be surgically implanted or connected externally to the patient receiving treatment. Clinicians use medical devices alone or in combination with drug therapies and surgery to treat patient medical conditions. For some medical conditions, medical devices provide the best, and sometimes the only, therapy to restore an individual to a more healthful condition and a fuller life. Examples of implantable medical devices include neuro stimulators, drug delivery pumps, pacemakers, defibrillators, diagnostic recorders, and cochlear implants. Some implantable medical devices provide therapies with significant power demands. To reduce the size of the power source and to extend the life of the power source, some of these implantable device can be recharged while implanted with a transcutaneous recharge signal.

Some implantable medical devices configured for recharging have a recharging coil that is external to the medical device housing and located remotely away from the medical device housing. Although a remote coil can be practicable for some situations, in other situations an external coil carried on the medical device would be preferred.

For the foregoing reasons there is a need for a rechargeable implantable medical device with an external recharging coil with improved attachments to the medical device.

SUMMARY OF THE INVENTION

A medical device has an external recharging coil attached to the medical device in an improved manner. In one embodiment, the recharging coil is carried on the proximal face of the medical device housing. In another embodiment, the recharging coil can either be carried on the proximal face of the medical device or detached from the proximal face and located remotely from the medical device. The recharging coil is electrically coupled through the housing electrical feedthroughs to electronics carried in the housing inner cavity. The recharging coil is also electrically coupled to a rechargeable power source carried in the housing inner cavity. The electronics are configured to perform a medical therapy or related purpose.

BRIEF DESCRIPTION OF THE DRAWINGS

FIG. 5b shows an exploded view of the rechargeable implantable neuro stimulator embodiment of FIG. 5a;

FIG. 6b shows an exploded view of the rechargeable implantable neuro stimulator embodiment of FIG. 6a;

FIG. 7b shows an exploded view of the rechargeable implantable neuro stimulator embodiment of FIG. 7a;

FIG. 8b shows an exploded view of the rechargeable implantable neuro stimulator embodiment of FIG. 8a;

DETAILED DESCRIPTION OF THE PREFERRED EMBODIMENTS

Figure 1:
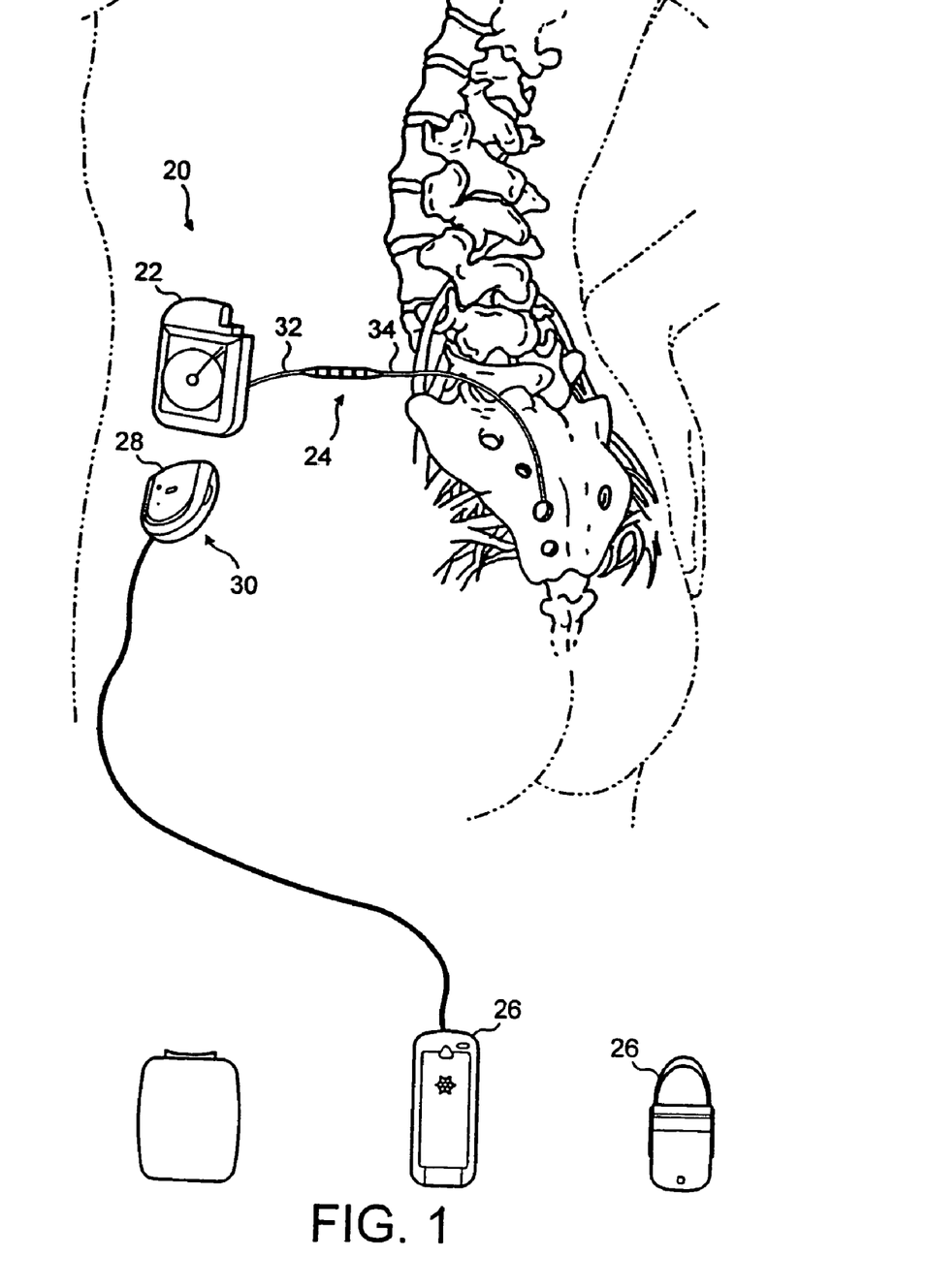
FIG. 1 shows an environment of a rechargeable implantable medical device.

FIG. 1 shows the general environment of one rechargeable implantable medical device 20 embodiment. A neuro stimulator 22 is shown in FIG. 1, but other embodiments such as drug delivery pumps, pacemakers, defibrillators, diagnostic recorders, and cochlear implants are also applicable. Implantable medical devices 20 are often implanted subcutaneously approximately one centimeter below the surface of the skin with an electrical lead 24 or catheter extending to one or more therapy sites. The rechargeable implantable medical device 20 is recharged with a recharging device such as a patient charger or programmer 26 that also has a charging capability.

Recharging an implanted medical device 20 generally begins with placing a recharging head 28 containing a primary recharging coil 30 on the surface of the patient's skin near the proximal side of the medical device. Some rechargers 26 have an antenna locator that indicates when the recharge head 28 is aligned closely enough with the implanted medical device 20 for adequate inductive coupling between the primary recharging coil 30 and the implanted medical device 20. The recharge power transfer signal is typically a frequency in the range from 5.0 KHz to 10.0 KHz and can be a higher frequency when the primary recharge coil 30 is remotely located froth the implanted medical device 20. The power transfer signal is converted by the implantable medical device 20 into regulated DC power that is used to charge the rechargeable power source. Once the recharge module fully charges the power source, the recharge module can be configured to serves as a power source for the implanted medical device while power is still being received. Telemetry can also be conducted between the recharger and the implanted medical device during recharging. Telemetry can be used to aid in aligning the recharger 26 with the implanted medical device 20, and telemetry can be used to manage the recharging process. Telemetry is typically conducted at a frequency in the range from 150 KHz to 200 KHz using a medical device telemetry protocol. For telemetry, the recharger 26 and implanted medical device 20 typically have a separate telemetry coil. Although, the recharge coil can be multiplexed to also serve as a telemetry coil.

Figure 2:
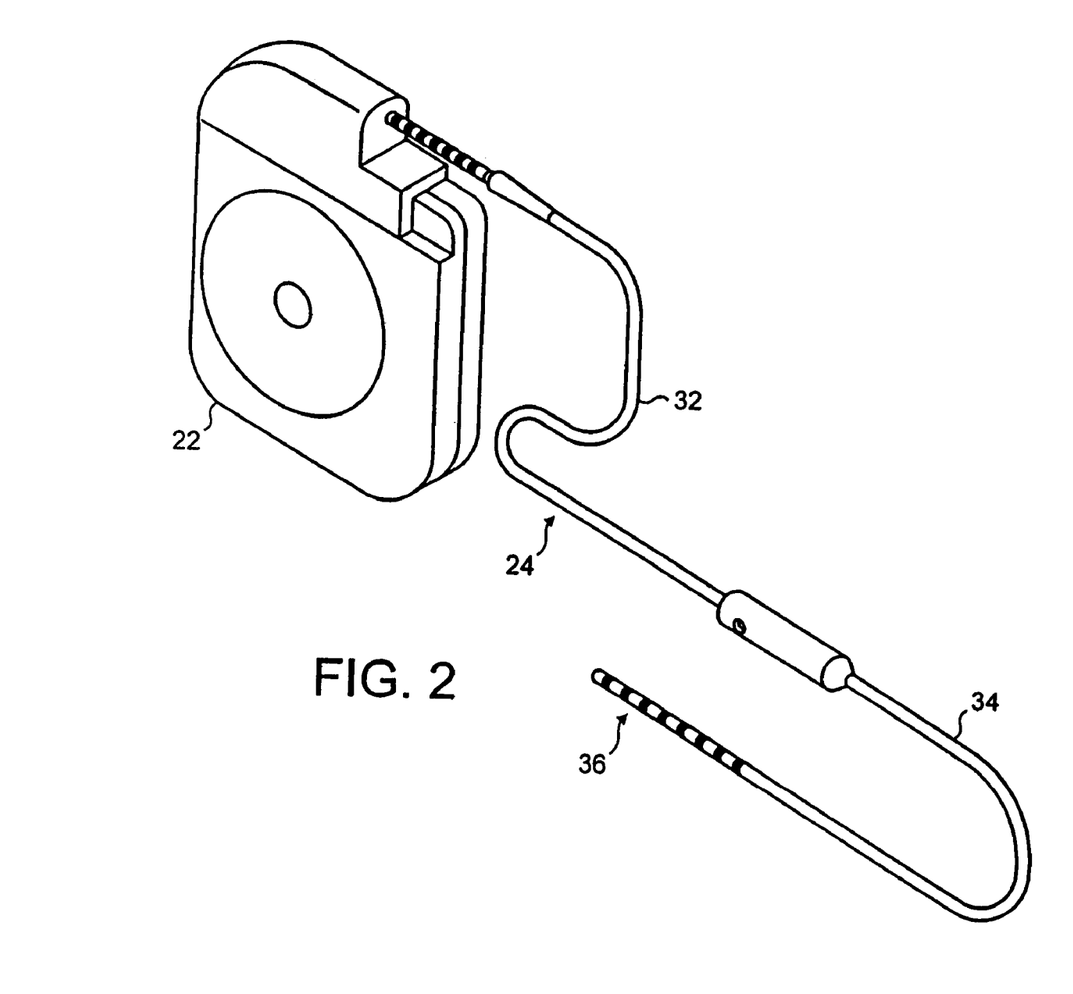
FIG. 2 shows an rechargeable implantable medical device neuro stimulator embodiment.
Figure 3:
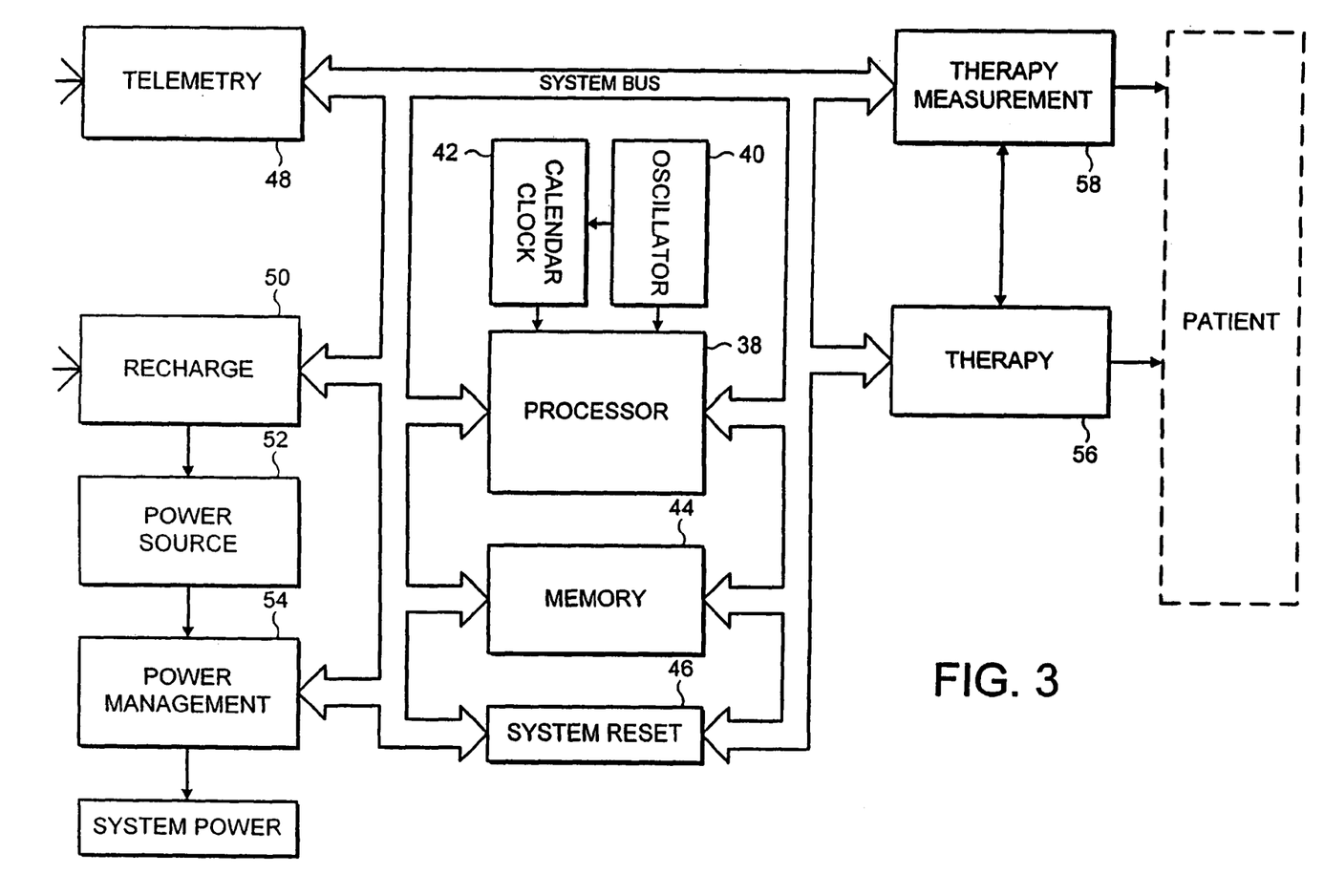
FIG. 3 shows an electronics block diagram of the rechargeable implantable medical device neuro stimulator embodiment.

FIG. 2 shows a rechargeable neuro stimulator 22 with a lead extension 32 and a stimulation lead 34 having electrical contacts 36 embodiment. FIG. 3 shows a neuro stimulator 22 electronics block diagram embodiment. The neuro stimulator 22 generates a programmable electrical stimulation signal. The neuro stimulator 22 electronics comprises a processor 38 with an oscillator 40, a calendar clock 42, memory 44, and system reset 46, a telemetry module 48, a recharge module 50, a power source 52, a power management module 54, a therapy module 56, and a therapy measurement module 58. All component of the neuro stimulator 22 are contained within or carried on the medical device 20.

Figure 4:
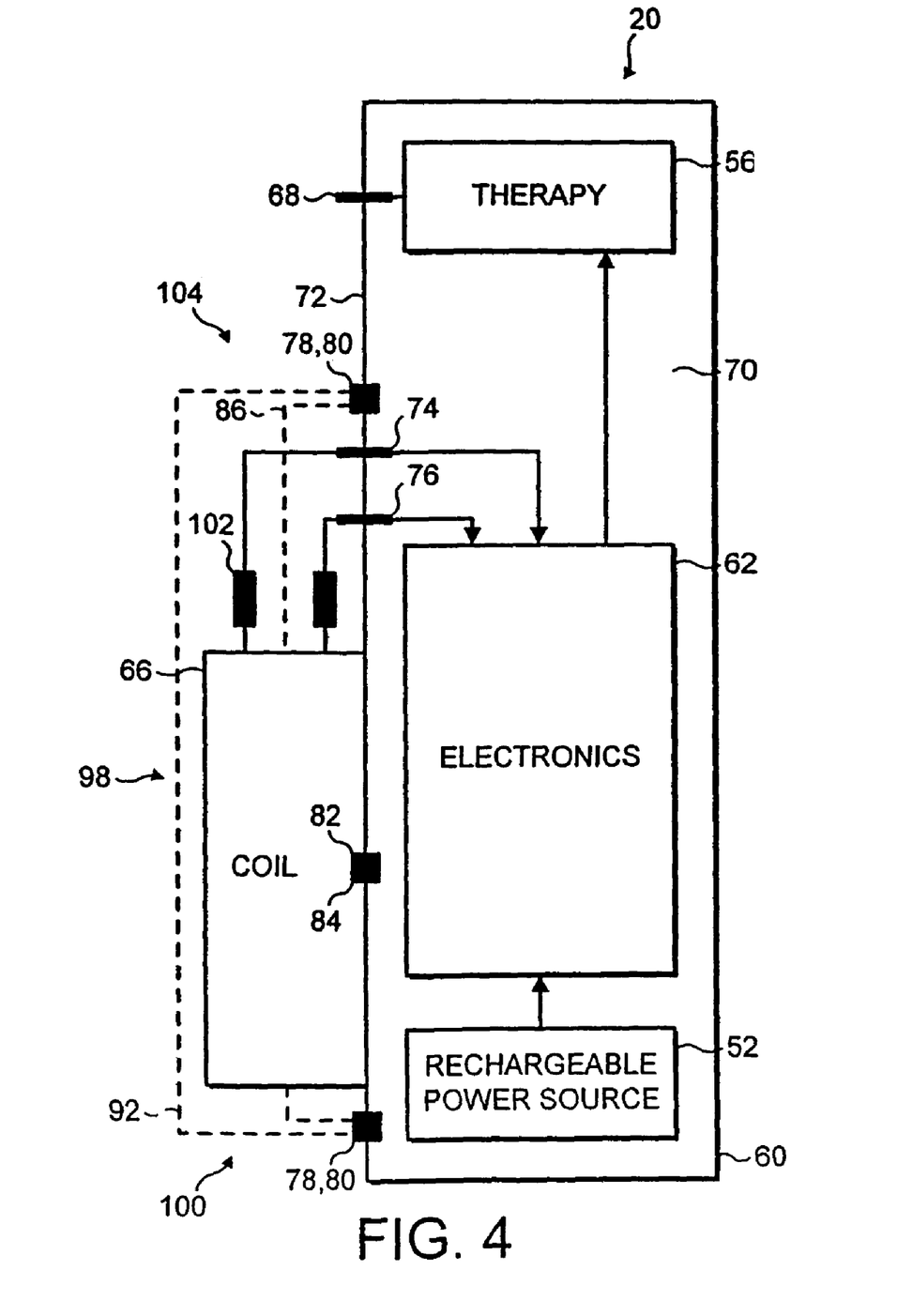
FIG. 4 shows a block diagram of an rechargeable implantable medical device embodiment.

FIG. 4 shows a block diagram of a rechargeable implantable medical device 20. The implantable medical device 20 with external recharging coil comprises a housing 60, electronics 62, a rechargeable power source 52, and a recharging coil 66. Some versions of the implantable medical device 20 will also have a therapy connection 68. The therapy connection 68 can be any type of therapy connection 68 such as a stimulation feedthrough, a drug infusion port, a physiological sensor, and the like. The housing 60 has an interior cavity 70, a proximal face 72, and at least one electrical feedthrough 74. The proximal face 72 when implanted is positioned towards the patient's skin. The electrical feedthroughs 74 include at least one recharge feedthrough 76 that can be located anywhere on the housing 60 such as located on the housing proximal face 72. The housing 60 is also configured to carry the recharging coil 66. In some embodiments the housing 60 has alignment details 78 and housing attachment details 80 to facilitate attaching the recharging coil 66 to the housing 60. Housing attachment details 80 can also serve as housing alignment detail 78 and vice versa. The housing alignment details 78 and housing attachment details 80 have geometries to accomplish their purpose such as latches, barbs, polymer anchors, and the like. The housing 60 is manufactured from a biocompatible material such as titanium, epoxy, ceramic, and the like. The housing 60 contains electronics 62.

The electronics 62 are carried in the housing interior cavity 70 and configured to perform a medical therapy such as neuro stimulation, cardiac pacing, defibrillation, drug delivery, or a related function such as data recording. The electronics 62 can also include a telemetry coil carried in the housing interior cavity 70 to receive telemetry message from sources such as a programmer 26. The electronics 62 are coupled to the rechargeable power source 52.

The rechargeable power source 52 is carried in the housing interior cavity 70 and coupled to the electronics 62. The rechargeable power source 52 can be a physical power source such as a spring or micro-generator, an electrical power source such as a capacitor or super capacitor, or a chemical power source such as a battery. The battery can be a hermetically sealed rechargeable battery such as a lithium ion (Li+) battery and the like. The rechargeable power source 52 can include both an electrical and chemical storage device. The rechargeable power source 52 is coupled to both the electronic 62 and can be coupled to both the electronics 62 and the recharging coil 66.

In one recharging coil 66 positioning embodiment, the recharging coil 66 is carried on the housing proximal face 72 and coupled through the housing electrical feedthrough 74 to the electronics 62 and rechargeable power source 52. The recharging coil 66 serves as a means for recharging the rechargeable power source 52. The recharging coil 66 is a wire coil having at least two leads configured to receive a recharging signal. The recharging coil 66 can have coil alignment details 82 and coil attachment details 84. The coil alignment details 82 can also serve as coil attachment details 84 and vice versa. The recharging coil 66 can be centrally located on the housing proximal face 72. The recharging coil 66 can be configured for multiplexing as a telemetry coil for communications between a programmer 26 and the implantable medical device 20. The recharging coil 66 is manufactured from a material with electromagnetic properties such as copper wire, copper magnet wire, copper litz woven wire, gold alloy, and the like. The recharge coil 66 can be manufactured from a wide variety of wire sizes such as wire diameters in the range from about 0.0127 cm (36 AWG, American Wire Gauge) to 0.0635 cm (22 AWG), or any other suitable diameter. The recharging coil 66 can be carried on the housing 60 by mechanical attachment, chemical attachment, or a combination of both mechanical and chemical attachment.

In one recharging coil 66 attachment embodiment, the recharging coil 66 is mechanically attached to the housing 60 by the coil alignment details 82 and coil attachment details 84 engaging housing alignment 78 and housing attachment details 80. In another embodiment, the recharging coil 66 can also be carried in a coil carrier 86. The coil carrier 86 has carrier alignment details 88 and carrier attachment details 90, and the alignment details 88 can also function as the attachment details 90 and vice versa. The coil carrier 86 permits the assembly of the coil 66 in the coil carrier 86 to facilitate alignment of the coil 66 and insert molding of the coil 66 and coil carrier 86 to the proximal face 72 of the medical device 20. The recharging coil 66 is placed in the coil carrier 86 and then the coil carrier 86 engages alignment 78 and attachment details 80 on the housing 60 to attach the recharging coil 66 and coil carrier 86 to the housing 60. The coil carrier 86 can be separate or the coil carrier 86 can be combined with another structure.

In another recharging coil 66 attachment embodiment, a coil cover 92 is used to cover the recharging coil 66 or cover the coil carrier 86 and recharging coil 66. The coil cover 92 has at least one cover alignment detail 94 and at least one cover attachment detail 96. The cover alignment details 94 can also serve as a cover attachment details 96 and vice versa. The coil cover 92 can be manufactured from an opaque material to facilitate product marking. The coil cover 92 can be configured to attach over the recharge coil 66 once the recharging coil 66 is attached to the housing 60. The coil cover 92 can also be configured to be used in combination with a coil carrier 86. The coil cover 92 can be attached after the coil carrier 86 once the coil 66 has been attached to the housing 60. The coil cover 92 can be placed over the coil carrier 86 and then both the coil cover 92 and coil carrier 86 attached to the housing 60. A coil assembly 98 can be created by combining the coil cover 92 with the coil carrier 86 containing the coil 66 and hermetically sealing the components together. Once the recharge coil 66 is mechanically attached to the housing 60 alone or in some versions with a coil carrier 86, or in other versions with a coil cover 92, a hermetic seal is typically formed.

The hermetic seal 100 is formed between components attached to the housing 60 and the housing 60 depending upon the version of the invention. When the recharging coil 66 is attached to the housing 60, the hermetic seal 100 is formed between the recharging coil 66 and the housing 60 to include the electrical connection 102 between the recharging coil 66 and the recharge feedthrough 76. When the recharging coil 66 is placed in a coil carrier 86 and attached to the housing 60, the hermetic seal 100 includes both the recharging coil 66 and the coil carrier 86. When a coil cover 92 is used, the hermetic seal 100 is formed between the coil cover 92 and the housing 60, and there can also be the an additional hermetic seal between the recharging coil 66 and the housing 60. The hermitic seal 100 can be formed in a wide variety of ways including applying a polymer to the coil 66 attached to the housing 60, placing the housing 60 including the attached coil 66 in a hermetic retention sleeve 104 and then forming a hermitic seal 100 around the opening where the housing 60 with attached coil 66 was inserted into the retention sleeve 104. The retention sleeve 104 can be of any biocompatible material suitable for the purpose such as silicone rubber, polysulfone, polyurethane, and the like. The recharging coil 66 can also be chemically attached to the housing 60.

In another recharging coil 66 attachment embodiment, the recharging coil 66 is chemically attached to the housing 60 using a biocompatible polymer. When the recharging coil 66 is chemically attached to the housing 60, the chemical attachment itself can form a hermetic seal 100 or a separate hermetic seal 100 can be formed between the recharging coil 66 and the housing 60. The recharging coil 66 can be attached to the housing 60 by encapsulation with a polymer. The recharging coil 66 can also be attached to the housing 60 by overmolding with a polymer. The overmolding can be accomplished in an in situ mold. Many versions of the implantable medical device 20 with external recharge coil 66 are possible.

Figure 5A:
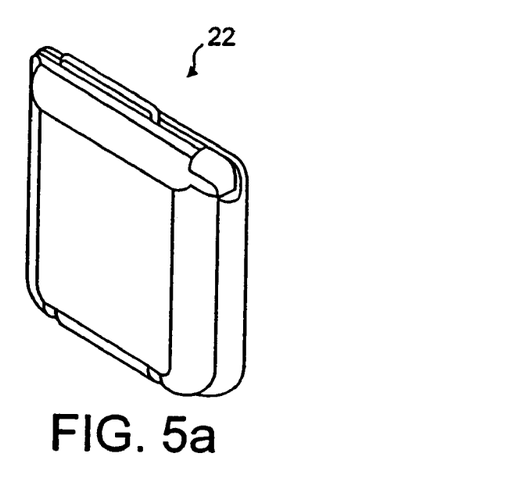
FIG. 5a shows a rechargeable implantable neuro stimulator embodiment.
Figure 5B:
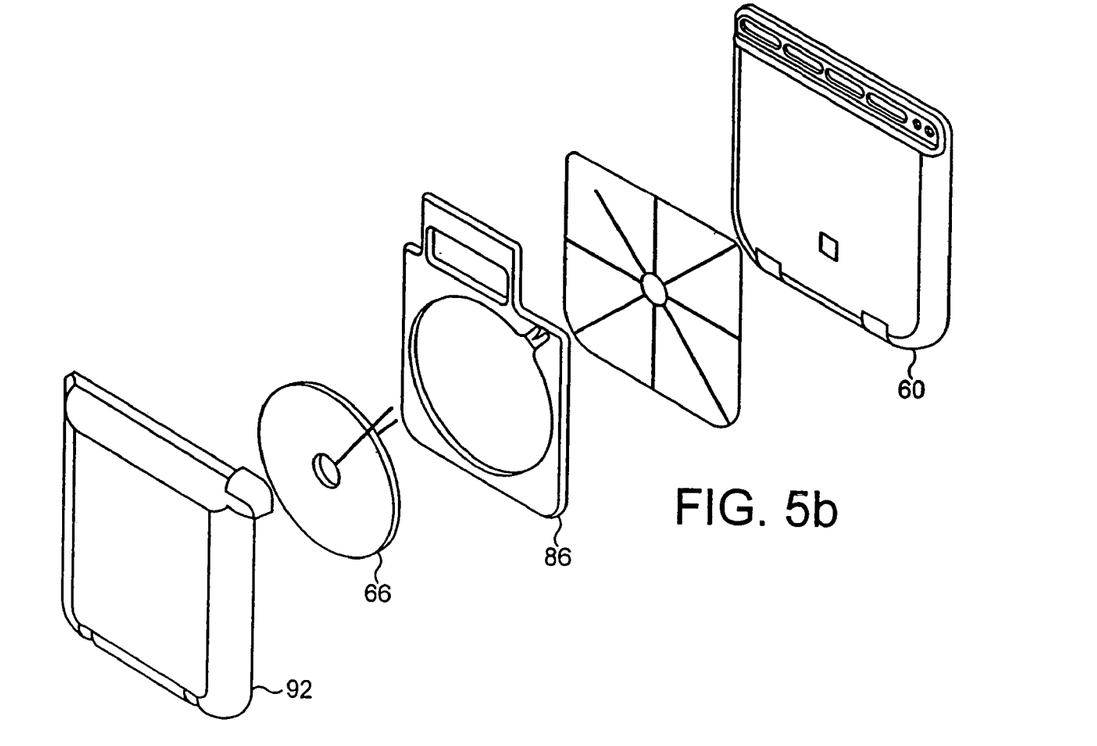
Figure 6A:
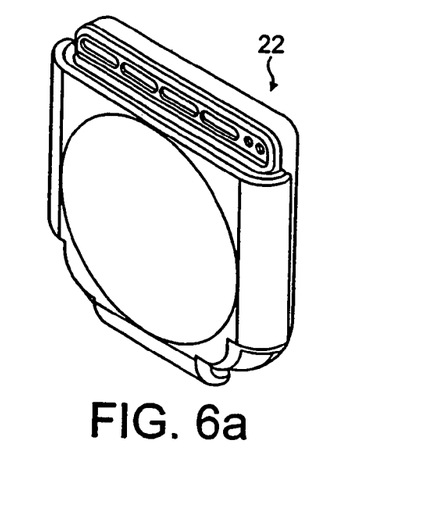
FIG. 6a shows a rechargeable implantable neuro stimulator embodiment.
Figure 6B:
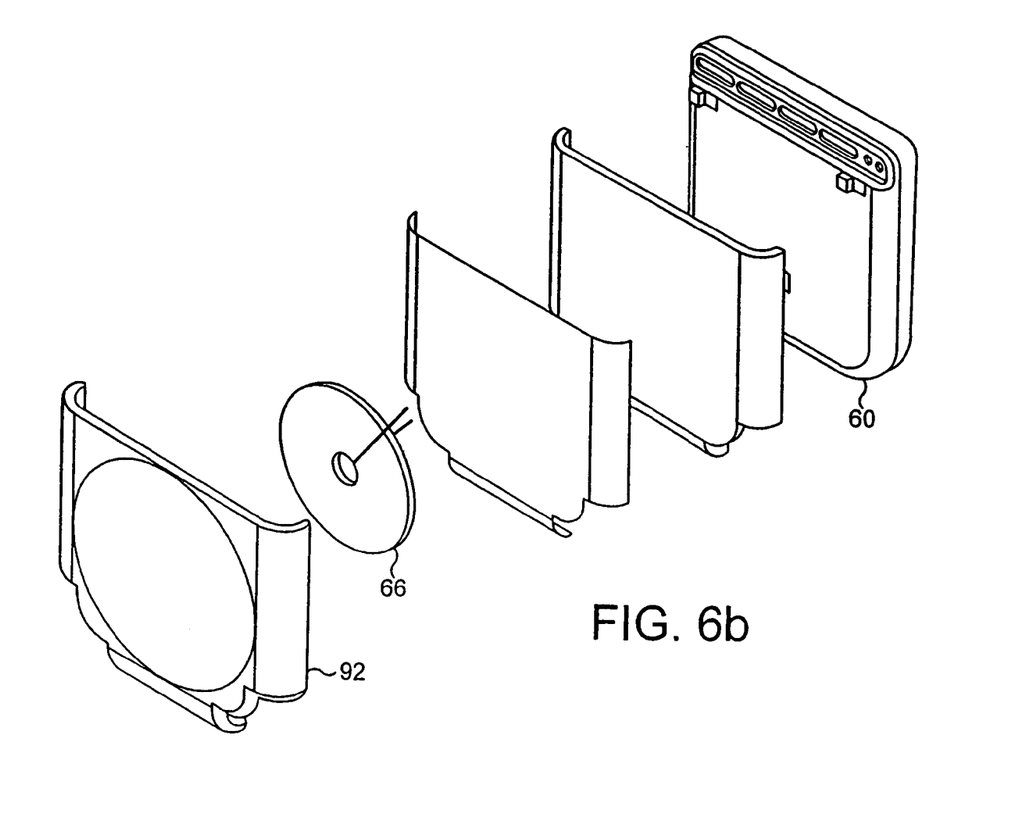
Figure 7A:
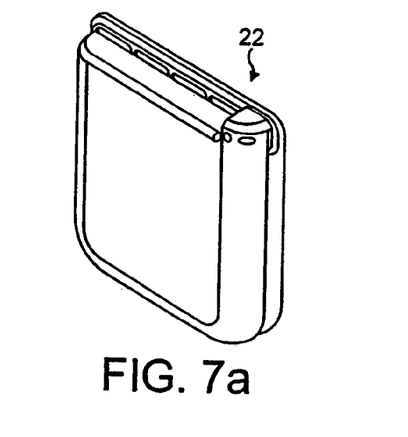
FIG. 7a shows a rechargeable implantable neuro stimulator embodiment.
Figure 7B:
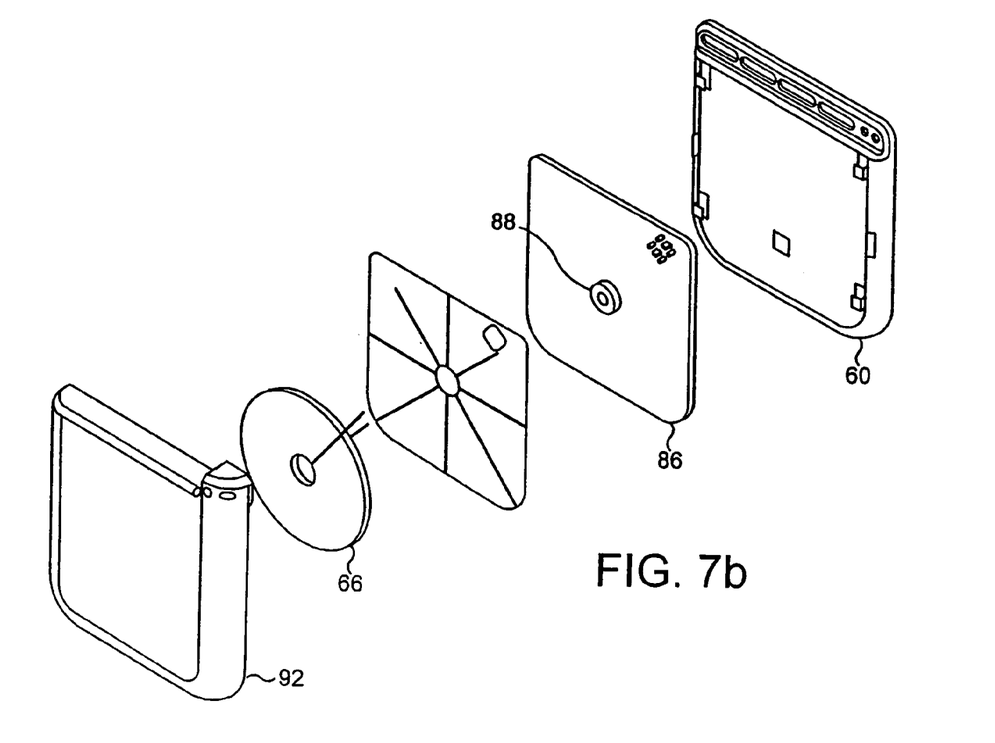
Figure 8A:
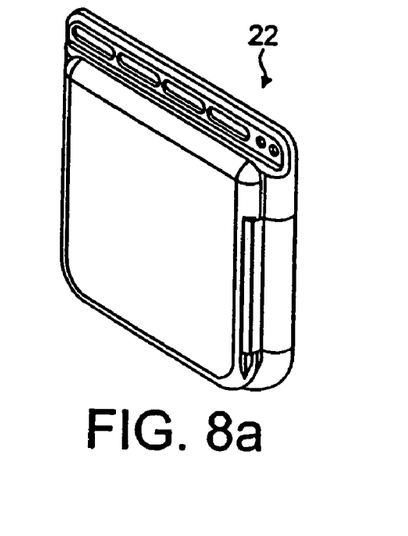
FIG. 8a shows a rechargeable implantable neuro stimulator embodiment.
Figure 8B:
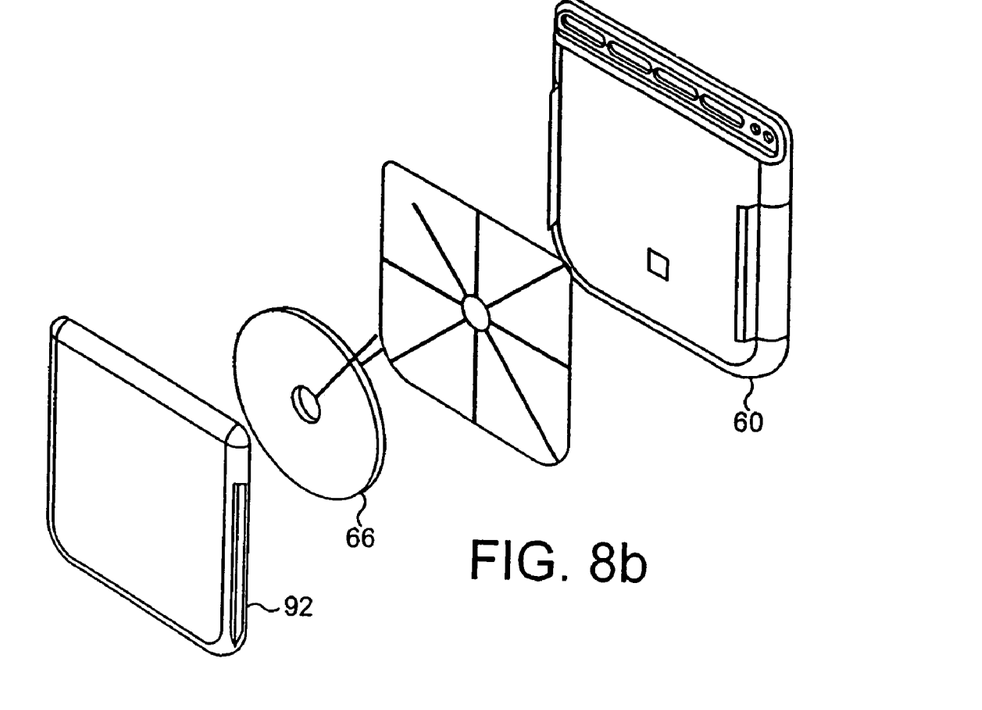

The following embodiments of the implantable medical device 20 with external coil 66 are discussed for illustrative purposes many other embodiments of the invention are possible. FIGS 5a-5b show an embodiment with a coil cover 92, and a coil carrier 86. FIGS. 6a-6b show an embodiment with another version of a coil cover 92. FIGS. 7a-7b show another embodiment with another version of a coil cover 92, another version of a coil carrier 86 with a carrier alignment detail 88 that engages the recharging coil 66. FIGS. 8a-8b show another embodiment with another version of a coil cover 92.

Figure 9A:
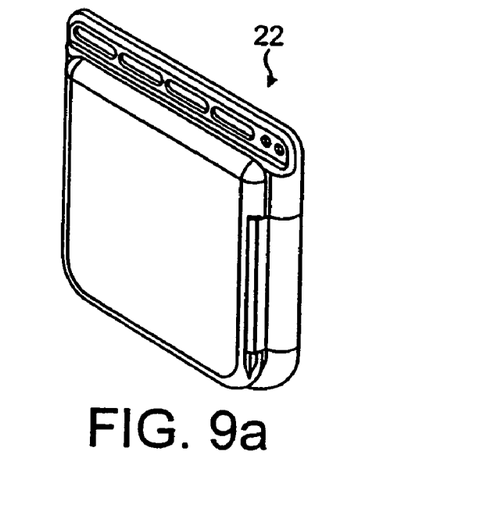
FIG. 9a shows an external recharging coil configured to be carried on the medical device embodiment.
Figure 9B:
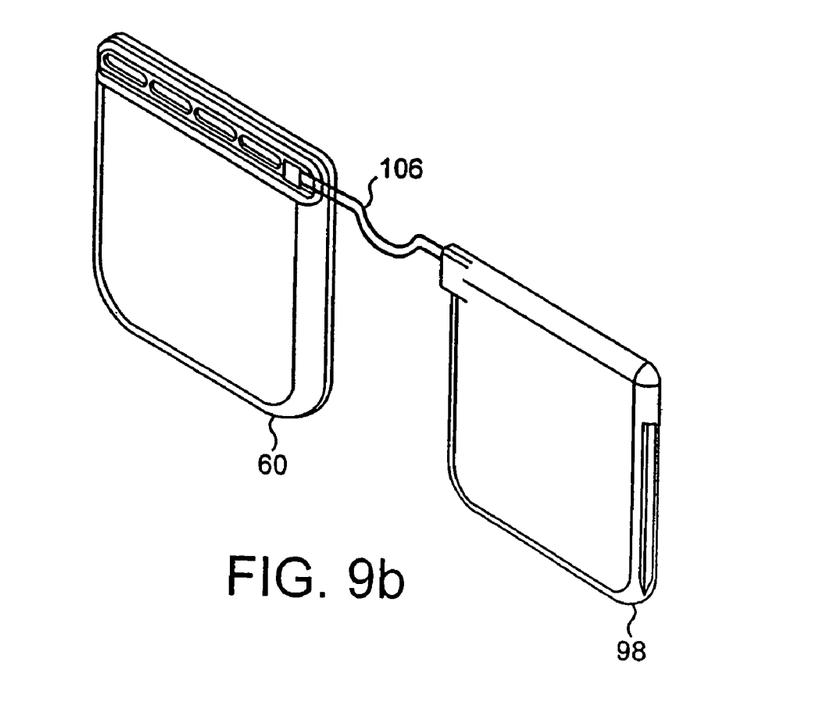
FIG. 9b shows an external recharging coil configured to be positioned remotely from the medical device embodiment; and, FIG. 10 shows a flowchart of a method of attaching an external recharging coil to an implantable medical device.

FIGS. 9a and 9b show another recharging coil 66 positioning embodiment. FIG. 9a shows an external recharging coil 66 configured to be carried on the medical device 20, and FIG. 9b shows an external recharging coil 66 configured to be positioned remotely from the medical device 20. The recharging coil 66 is carried in a coil assembly 98 that is hermetically sealed. The coil assembly 98 is configurable to a first position on the proximal face 72 of the medical device 20 and coupled through the housing electrical feedthrough 74 to the electronics 62. When positioned on the proximal face 72, the coil assembly 98 is attached with a mechanical fastener such as a spring rail and groove. The coil assembly 98 is also configurable to a second position remote from the medical device 20 and coupled with a remote lead 106 through the housing electrical feedthrough 74 to the rechargeable power source 52. When the coil assembly 98 is positioned remote from the medical device 20, the mechanical fastener can be removed. With this embodiment, the implanting clinician can decide whether the recharging coil 66 should be attached to the proximal face 72 of the medical device 20 or positioned remotely from the medical device 20 for benefits such as ease of access by the patient. Positioning the recharging coil 66 away from the housing 60 also can reduce eddy currents induced into the housing 60 during recharging.

Figure 10:
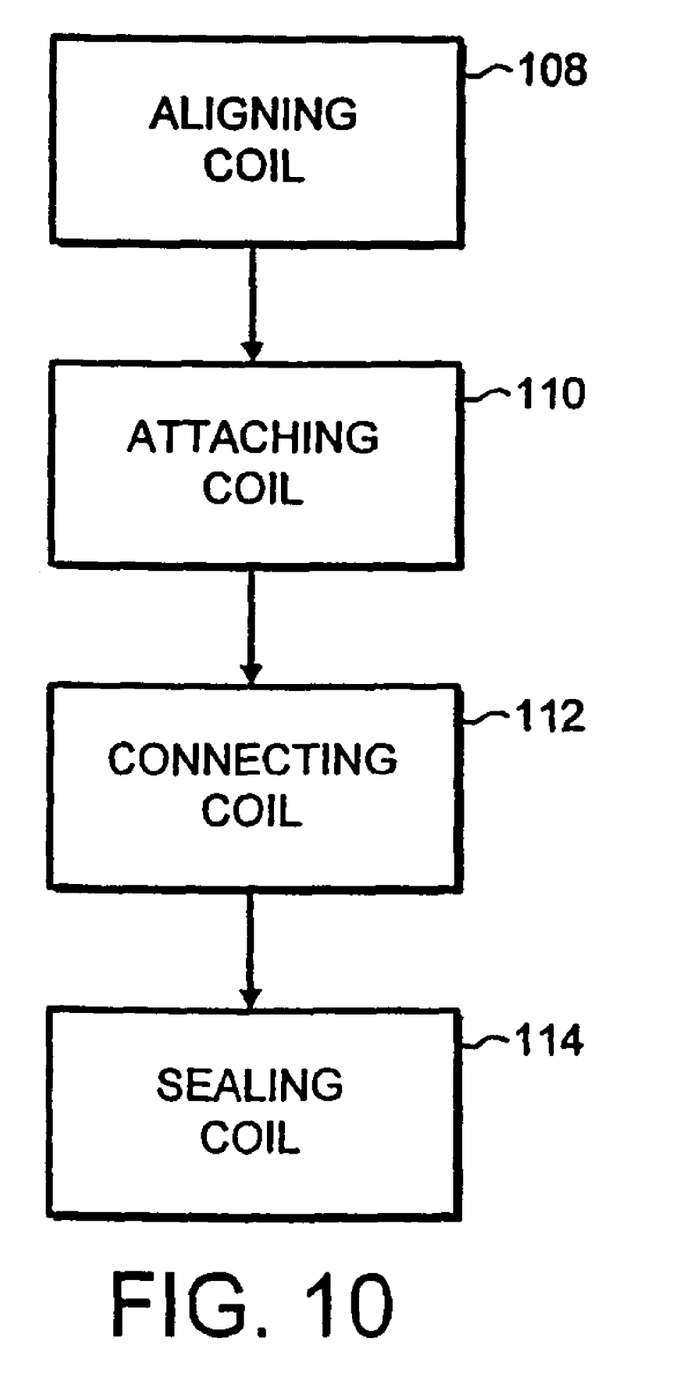

FIG. 10 shows a method of attaching an external recharging coil 66 to an implantable medical device 20. The method comprises the following elements. Aligning 108 the recharging coil 66 by having at least one coil alignment detail 82 with at least one housing alignment detail 78 located on a housing proximal face 72. Attaching 110 the recharging coil 66 by coupling at least one coil attachment detail 84 to at least one housing attachment detail 80. Connecting 112 electrically the recharging coil 66 to a coil feedthrough 76 carried on the housing 60. Sealing 114 hermetically the recharging coil 66 to the housing proximal face 72. The method can also include covering a recharging coil 66 substantially with a coil cover 92 having at least one cover attachment detail 96 configured to couple with at least one housing attachment detail 80. When a coil cover 92 is used, at least a portion of the hermetic seal 100 is typically formed after the coil cover 92 is attached to the housing 60.

Another version of the method for attaching an external recharging coil 66 to an implantable medical device 20 uses a coil carrier 86. The coil carrier 86 can be a separate structure or can be another structure such as a coil cover 92 that also functions as a coil carrier 86. The coil carrier 86 assists in aligning the recharging coil 66 with the housing proximal face 72, and can simplify assembly processes. Aligning the recharging coil 66 having at least one coil alignment detail 82 with at least one carrier alignment detail 88. Aligning the coil carrier 86 having at least one carrier alignment detail 88 with at least one housing alignment detail 78. Attaching the coil carrier 86 containing the recharging coil 66 by coupling at least one carrier attachment detail 90 to at least one housing attachment detail 80. Connecting electrically the recharging coil 66 to a coil feedthrough 76 carried on the housing 60. Sealing hermetically the recharging coil 66 to the housing proximal face 72. The method can also include covering the coil carrier 86 contain the recharging coil 66 substantially with a coil cover 92 having at least one cover attachment detail 96 configured to couple with at least one housing attachment detail 80. When a coil cover 92 is used, at least a portion of the hermetic seal 100 is formed after the coil cover 92 is attached to the housing 60.

Thus, embodiments of a rechargeable implantable medical device 20 with an improved external recharging coil attachment are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. An implantable medical device adapted to be charged with an external recharging coil, comprising:
    a housing having an interior cavity, a proximal face, and an electrical feedthrough;
    electronics carried in the housing interior cavity, the electronics configured to perform a medical therapy;
    a rechargeable power source carried in the housing interior cavity and electrically coupled to the electronics; and,
    a recharging coil having a major plane and being centrally located and substantially carried exterior to the proximal face of the housing and electrically coupled through the housing electrical feedthrough to the electronics and rechargeable power source, the proximal face of the housing being co-planar with the major plane of the recharging coil.

2. The implantable medical device as in claim 1 wherein the electrical feedthrough includes a recharge feedthrough located on the proximal face of the housing.

3. The implantable medical device as in claim 1 wherein the recharging coil is mechanically attached to the housing.

4. The implantable medical device as in claim 1, further comprising at least one housing attachment detail.

5. The implantable medical device as in claim 1, further comprising a coil cover that carries the recharging coil and attaches to the housing.

6. The implantable medical device as in claim 5, further comprising at least one cover alignment detail.

7. The implantable medical device as in claim 5, further comprising at least one cover attachment detail.

8. The implantable medical device as in claim 5, further comprising a biocompatible polymer to create a hermetic seal between the coil cover and the housing.

9. The implantable medical device as in claim 5, further comprising a coil alignment carrier for carrying the coil, the coil alignment carrier positioned between the coil cover and the housing.

10. The implantable medical device as in claim 9 wherein the coil alignment carrier is hermetically sealed to the coil cover to form a coil assembly.

11. The implantable medical device with external recharging coil as in claim 1 wherein the recharging coil is attached to the housing by encapsulation with a polymer.

12. The implantable medical device as in claim 1 wherein the recharging coil is attached to the housing by overmolding with a polymer.

13. The implantable medical device as in claim 12, wherein the overmolding is accomplished in situ.

14. The implantable medical device as in claim 1 wherein the recharging coil is mechanically attached to the housing with a retention sleeve.

15. The implantable medical device as in claim 14 wherein the retention sleeve is hermetically sealed to the housing.

16. The implantable medical device as in claim 1 wherein the rechargeable power source is an electrical storage device.

17. The implantable medical device as in claim 1 wherein the rechargeable power source is a chemical storage device.

18. The implantable medical device as in claim 1 further comprising a telemetry coil carried in the housing interior cavity.

19. The implantable medical device as in claim 1 wherein the recharging coil is configured for multiplexing as a telemetry coil for communications between a programmer and the electronics.

20. The implantable medical device as in claim 1 wherein the medical device is selected from the group consisting of: a neuro stimulator, a pacemaker, a defibrillator, drug delivery pump, and a diagnostic recorder.

21. An implantable medical device adapted to be charged with an external recharging coil, comprising:
   a housing having an interior cavity, a proximal face, and an electrical feedthrough;
   electronics carried in the housing interior cavity, the electronics configured to perform a medical therapy;
   a rechargeable power source carried in the housing interior cavity and electrically coupled to the electronics; and,
   means for recharging having a major plane and being carried exterior to the proximal face of the housing and electrically coupled through the housing electical feedthrough to the eletronics and the rechargeable power source; and
   means for attaching the means for recharging to a position centrally located and substantially carried on the housing proximal face, the proximal face of the housing being co-planar with the major plane of the recharging coil.

* * * * *